US012706211B2

(12) United States Patent
Brazil et al.

(10) Patent No.: US 12,706,211 B2
(45) Date of Patent: Aug. 11, 2026

(54) NETWORK HOSTED SYSTEM FOR SELECTING PRODUCTS FOR PATIENT USE BASED ON INPUT DIAGNOSTIC DATA

(71) Applicant: Global Healing Arts LLC, Indian Wells, CA (US)

(72) Inventors: Ronald Douglas Brazil, San Juan Capistrano, CA (US); James E. Thomas, Waverly, MN (US); Mark Ferrel, Bishopville, MD (US)

(73) Assignee: Global Healing Arts LLC, Indian Wells, CA (US)

( * ) Notice: Subject to any disclaimer, the term of this patent is extended or adjusted under 35 U.S.C. 154(b) by 791 days.

(21) Appl. No.: 16/578,274

(22) Filed: Sep. 20, 2019

(65) Prior Publication Data

US 2020/0020449 A1 Jan. 16, 2020

Related U.S. Application Data

(63) Continuation-in-part of application No. 15/283,386, filed on Oct. 1, 2016, now abandoned.

(51) Int. Cl.

*G16H 50/20* (2018.01)
*G16H 10/20* (2018.01)
*G16H 10/60* (2018.01)
*G16H 15/00* (2018.01)
*G16H 50/70* (2018.01)

(52) U.S. Cl.

CPC ............. *G16H 50/20* (2018.01); *G16H 10/20* (2018.01); *G16H 10/60* (2018.01); *G16H 15/00* (2018.01); *G16H 50/70* (2018.01)

(58) Field of Classification Search

CPC ........ G16H 50/20; G16H 10/20; G16H 10/60; G16H 15/00; G16H 50/70; G16H 70/40; G16H 20/10

See application file for complete search history.

(56) References Cited

U.S. PATENT DOCUMENTS

| | | | | |
|---|---|---|---|---|
| 2015/0287122 A1* | 10/2015 | Mak | .................... | G06F 3/04883 705/26.7 |
| 2015/0324534 A1* | 11/2015 | Ruben | .................... | G16H 15/00 705/2 |
| 2016/0283921 A1* | 9/2016 | Ramanathan | .......... | G16H 10/60 |
| 2017/0220766 A1* | 8/2017 | Mangione | ............. | G16H 20/90 |

* cited by examiner

*Primary Examiner* — Benjamin J Klein
*Assistant Examiner* — Daniel Tehrani
(74) *Attorney, Agent, or Firm* — Buchalter; Michael Tait

(57) ABSTRACT

A network-hosted product selection system includes a first server having at least one connected data repository, the first server including a non-transitory medium coupled thereto, the non-transitory medium including instructions for the first server to accept a digitally coded patient state diagnosis model from a connected input device, parse said diagnosis model for information, compare results with information derived from individual ones of product data models, the product data models including parse able tags weighing efficacy in treatment of one or more medical conditions and or symptoms derived from the patient state diagnosis model, select one or more product data models weighing high in efficacy based on at least collective tag weight and displaying products and associated transactional data and product consumption recommendation data.

20 Claims, 6 Drawing Sheets

501

Communication_Input Layer
(Client File Transfer-Input)

502

Parsing Layer (Model Readout)

503

Information Processing Layer
(Search Algorithm)

504

Data Presentation Layer
(Visual/Audio Interface
Terminal/Server/End Device)

NETWORK HOSTED SYSTEM FOR SELECTING PRODUCTS FOR PATIENT USE BASED ON INPUT DIAGNOSTIC DATA

This application is a continuation-in-part application of U.S. Ser. No. 15/283386, filed on Oct. 1, 2016, the disclosure of which is incorporated by reference in its entirety.

FIELD OF INVENTION

Recommendation system and network for matching a patient's medical needs to an appropriate cannabis strain, cannabis extract, or other product derived from processing of the raw plant matter, and processes for extraction of compounds from plant matter such as cannabis. The present invention is described in enabling detail using the following examples, which may describe more than one relevant embodiment falling within the scope of the present invention.

BACKGROUND

Cannabis has been used medicinally for many years for a variety of different medicinal uses. Historically, cannabis regarded by many medical professionals as unique; having the ability to counteract pain resistant to opioid analgesics, in conditions such as spinal cord injury, and other forms of neuropathic pain including pain and spasm in multiple sclerosis. Cannabis has a number of other known medicinal uses including but not limited to reducing nausea, increasing appetite, reducing pain and inflammation, controlling epileptic seizures, and possibly even treating mental illness and addictions. And as cannabis becomes more prevalent in the United States and globally new medicinal uses are discovered every day.

The principle cannabinoid compounds commonly present in herbal cannabis are the cannabinoid acids $\Delta^9$ tetrahydrocannabinolic acid (THCA) and cannabidiolic acid (CBDA), with small amounts of the corresponding neutral cannabinoids, respectively $\Delta^9$ tetrahydrocannabinol (THC) and cannabidiol (CBD). Cannabidiol was formerly regarded as an inactive constituent, however there is emerging evidence that it has pharmacological activity, which is different from that of THC in several respects.

In addition to these major cannabinoids, herbal cannabis may contain other minor cannabinoids. These may be intermediates in the biosynthesis of the major cannabinoids and hence exist at only low levels in the plant as they are constantly undergoing further biotransformation once they are formed. An example of such a cannabinoid is cannabigerol (CBG). Other minor cannabinoids may represent the end point of an alternative biosynthetic pathway to that leading to the formation of the major cannabinoids $\Delta^9$ THC and CBD. These cannabinoids are frequently relatively more abundant in the plant, an example being cannabichromene (CBC). Some cannabis strains may contain minor cannabinoids that are the result of a yet another biosynthetic pathway to that leading to the formation of other cannabinoids, such as Tetrahydrocannabivarin (THCV) and Cannabidivarin (CBDV)

In addition to cannabinoids, cannabis strains may contain over 120 terpene compounds including but not limited to, α-Pinoline, Myrcene, Limonene, β-Caryophyllene, Linalool, Humulene, Ocimene, and Terpinolene. Terpenes often have synergistic effects with Cannabinoid compounds, as well as, benefits of their own. For instance, α-Pinoline is thought to affect alertness, memory retention and counter some effects of THC. It may treat asthma, pain, inflammation, ulcer, anxiety, and cancer. Myrcene is thought to have relaxing and sedation effects. It may treat insomnia, pain and inflammation. Limonene is thought to elevate mood and relieve stress. It may treat anxiety, depression, inflammation, pain and cancer. β-Caryophyllene is thought to relieve stress. It may also treat pain, anxiety/depression, and ulcers. Linalool is thought to be a mood enhancer and a sedative. It may treat anxiety, depression, insomnia, pain, inflammation and neurodegenerative diseases. Humulene is thought to treat inflammation. Ocimene may treat antiviral, anti-fungal, antiseptic, decongestant, antibacterial. Terpinolene is thought to be relaxing. It may be an antioxidant, a sedative, antibacterial, anti-fungal and anti-cancer.

There are literally hundreds and thousands of cannabis varieties and strains, each has a unique cocktail of cannabinoids and terpenes. This cocktail of terpenes and cannabinoids contributes to a cannabis strain's use and efficacy in treating medical, physiological and psychological conditions, its taste, its smell, and its organoleptic feel when consuming it.

While much of the research has sought to create purified forms of certain of the cannabinoids present in herbal cannabis as being useful as active pharmaceutical agents, the purification process described herein seeks to do the opposite because isolated cannabinoids are not often as effective as medical treatments that include natural extract from the whole plant. Utilizing the full spectrum of therapeutic compounds is often referred to as the entourage effect, where synergistic effects between the unique blend of cannabinoids and terpenes create a better treatment, and a better user experience.

Additionally, given the wide spectrum of cannabis strains on the market, cannabis users need a better way to categorize cannabis by its medicinal properties, as well as, by its taste, smell, and feel in order to find the right cannabis strain to treat their medical conditions.

SUMMARY

A recommendation system and network for matching a patient's medical needs and personal preferences to an appropriate cannabis strain, cannabis extract thereof, or other cannabis product derived therefrom, using a software program.

A process of selecting an appropriate cannabis strain, cannabis extract thereof, or other cannabis product derived therefrom by (i) engaging a software program; (ii) inputting a patient's medical condition and personal preferences for taste and means of ingestion into the software program; and (iii) software program identifies one or more appropriate cannabis products for the patient.

A network based cannabis product recommendation system for patients and/or users including a network connected node executing a set of software instructions from a non-transitory medium the instructions executable to cause the node to perform the tasks (i) receiving as input in a file transfer, an electronic data file representing a patient medical profile model from a device having data transfer and or data sync access to the network connected node; (ii) parsing the data file representing the patient medical profile model to identify and aggregate object and attribute data representing at least the current medical condition(s) of the patient, the current medical symptoms exhibited by the patient, the current treatment regimens prescribed to the patient, and the current side effects of treatment regimens suffered by the patient; and (iii) searching, using the aggregated patient model object and attribute data, in a network-connected data repository and identifying one or more cannabis product models having object and attribute data pre-equated for efficacy in treatment of one or more conditions represented by object and attribute data generally included in the received patient medical profile.

According to embodiments of the invention, a network-hosted product selection system is provided including a first server on the network, the first server having at least one connected data repository, the first server including a non-transitory medium coupled thereto, the non-transistory medium including instructions for the first server to accept a digital executable file in the form of a digitally coded patient state diagnosis model from a connected input communications and or memory device, execute and parse said diagnosis model for information, compare parsed information with information derived from individual ones of product data models, the product data models including parse able tags weighing efficacy in treatment of one or more medical conditions and or symptoms derived from the patient state diagnosis model, select one or more than one of the product data models from the connected data repository based on at least collective tag weight resulting from comparison as preferred products for patient use, and, presenting a human-readable display listing the one or more than one products and associated transactional data and product consumption recommendation data.

A network based cannabis product recommendation system for patients and/or users including a network connected node executing a set of software instructions from a non-transitory medium the instructions executable to cause the node to perform the tasks (i) receiving as input in a file transfer, an electronic data file representing a patient medical profile model from a device having data transfer and or data sync access to the network connected node; (ii) parsing the data file representing the patient medical profile model to identify and aggregate object and attribute data representing at least the current medical condition(s) of the patient, the current medical symptoms exhibited by the patient, the current treatment regimens prescribed to the patient, and the current side effects of treatment regimens suffered by the patient; and (iii) searching, using the aggregated patient model object and attribute data, in a network-connected data repository and identifying one or more cannabis product models having object and attribute data pre-equated for efficacy in treatment of one or more conditions represented by object and attribute data generally included in the received patient medical profile; and (iv) returning a list of executable files or links to one or more than one cannabis product profile models to the node for display.

A process of extracting cannabinoids and terpenes to substantially preserve the original terpene/cannabinoid profile using the steps of: (i) select dried, ground dried cannabis; (ii) mix the ground cannabis powder with ethanol to create a cannabis slurry; (iii) cryogenically freeze the cannabis slurry for an extended period of time using a cryogenic freezer; (iv) separate the ethanol solution from the ground cannabis; (v) wash the remaining ground cannabis with cryogenically frozen ethanol; (vi) filter the ethanol wash and ethanol from original cannabis slurry, which now contain extracted cannabinoids and terpenes; and (vii) evaporate the ethanol from the cannabis leaving a thick cannabis oil and such that the cannabinoid and terpenes profile of the selected cannabis is substantially preserved and/or extracted at increased rates.

A process of extracting cannabinoids and terpenes to substantially preserve the original terpene/cannabinoid profile using the steps of: (i) Selecting cannabis flower with desirable terpene and cannabinoid profile; (ii) drying cannabis flower; (iii) grind cannabis flower to a coarse powder; (iv) mix the ground cannabis powder with ethanol to create a cannabis slurry; (v) freeze the cannabis slurry at −130 F to −170 F for between 12 to 72 hours using a cryogenic freezer; (vi) separate the ethanol solution from the ground cannabis; (vii) wash the remaining ground cannabis with cryogenically frozen ethanal −130 to −170 F between 4 and 10 times; (viii) collect ethanol wash and ethanol from original cannabis slurry, which now contain extracted cannabinoids and terpenes; (ix) filter the ethanol mix using one or more filters; (x) evaporate the cannabis wash leaving a thick cannabis oil containing the extracted cannabinoids and terpenes; (xi) optionally cure the cannabis oil by stirring the oil for 6-36 hours at the desired temperature, between 80 F and 180 F, leaving a think residue; and (xii) dry the cannabis residue in a vacuum oven to until oil can be tested and in compliance with California state standards.

A process of extracting cannabinoids and terpenes to substantially preserve the original terpene/cannabinoid profile using the steps of: (i) Selecting cannabis flower with desirable terpene and cannabinoid profile; (ii) drying cannabis flower; (iii) grind cannabis flower to a coarse powder; (iv) mix the ground cannabis powder with ethanol to create a cannabis slurry; (v) freeze the cannabis slurry at −165 F to −175 F for approximately 48 hours using a cryogenic freezer; (vi) separate the ethanol solution from the ground cannabis; (vii) wash the remaining ground cannabis with cryogenically frozen ethanal −165 F to −175 F between 4 and 10 times; (viii) collect ethanol wash and ethanol from original cannabis slurry, which now contain extracted cannabinoids and terpenes; (ix) filter the ethanol mix using one or more filters; (x) evaporate the cannabis wash leaving a thick cannabis oil containing the extracted cannabinoids and terpenes; (xi) optionally cure the cannabis oil by stirring the oil for 6-36 hours at the desired temperature leaving a think residue; and (xii) dry the cannabis residue in a vacuum oven to until oil can be tested and in compliance with California state standards.

Any process of extracting cannabinoids and terpenes described herein, wherein the method of freezing is a cryogenic freezer, such that a consistent subzero temperature can be maintained for up to 72 hours.

Any process of extracting cannabinoids and terpenes described herein, wherein the ratio of cannabis flower to ethanol in the cannabis slurry is 1:5 (lb/gallon), 1:4 (lb/gallon), 1:3 (lb/gallon), 1:2 (lb/gallon), 1:1 (lb/gallon), or 2:1 (lb/gallon).

Any process of extracting cannabinoids and terpenes described herein, wherein the ratio of cannabis flower to ethanol wash is 1:5 (lb/gallon), 1:4 (lb/gallon), 1:3 (lb/gallon), 1:2 (lb/gallon), 1:1 (lb/gallon), or 2:1 (lb/gallon).

Any process of extracting cannabinoids and terpenes described herein, wherein the cannabis flower is washed with 1 to 10 washes of in the ratio of cannabis to ethanol wash 4:1 (lb/gallon), 3:1 (lb/gallon), 2:1 (lb/gallon), 1:1 (lb/gallon), or 1:2 (lb/gallon).

Any process of extracting cannabinoids and terpenes described herein, wherein the cannabis slurry is frozen to −130 F, −135 F, −140 F, −145 F, −150 F, −155 F, −160 F, −165 F, −170 F, −175 F, −180 F, −185 F, or −190 F.

Any process of extracting cannabinoids and terpenes described herein, wherein the cannabis slurry is frozen or soaking for approximately 6 hrs, 12 hrs, 18 hrs, 24 hrs, 30 hrs, 36 hrs, 42 hrs, 43 hrs, 44 hrs, 45 hrs, 46 hrs, 47 hrs, 48 hrs, 49 hrs, 50 hrs, 51 hr, 52 hrs, 53 hrs, 54 hrs, 60 hrs, 66 hrs, or 72 hrs.

Any process of extracting cannabinoids and/or terpenes described herein, wherein the cannabis is ground as fine as coffee grounds, particles having an average diameter of 580 microns.

Any process of extracting cannabinoids and terpenes described herein, wherein the cannabis is filtered through a one or more coffee filters, or one or more filter having a porous diameter of 20±5 microns, 20±1 microns or more preferably 20 microns Any process of extracting cannabinoids and/or terpenes described herein, wherein the cannabis is cured at temperature of 173±5 F, 173±1 F, or more preferably 173 F.

DETAILED DESCRIPTION

Definitions

Figure 1:
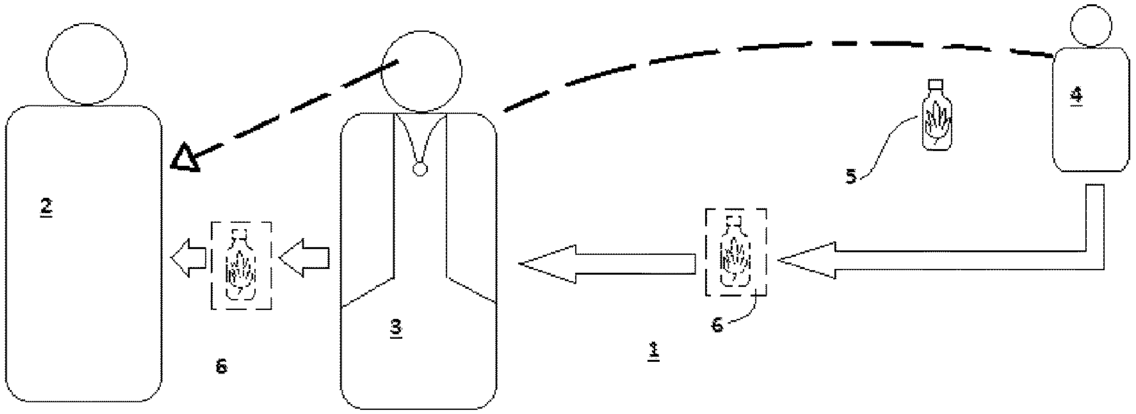
FIG. 1 is a block diagram depicting a method of medical cannabis recommendation.

Before describing the subject matter herein, it should be noted that it is not limited to the described recommendation systems, extracts and methods, as well as the terminology used herein for describing particular embodiments is not intended to be limiting. Unless defined otherwise, all technical and scientific terms used herein have the meaning as commonly understood by one of ordinary skill in the art to which this invention pertains. Although any methods and materials similar or equivalent to those described herein can be used in the practice or testing of the invention, particular methods and materials are now described.

As used herein, the following terms and phrases shall have the meanings set forth below. Unless defined otherwise, all technical and scientific terms used herein have the same meaning as commonly understood to one of ordinary skill in the art.

The term "cannabis plants" as used herein, the term "plant" refers to plants in the genus of cannabis and plants derived thereof. Such as cannabis plants produced via asexual reproduction and via seed production.

As used herein, the term "cannabis plant matter" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "above-ground" part, also often referred to as the "shoots", and the "below-ground" part, also often referred to as the "roots". Plant part may also include certain extracts such as kief or hash which includes cannabis trichomes or glands.

The term "raw cannabis flower" means unprocessed cannabis flower bud. Raw cannabis flower is typically dried without heat for the purposes of being consumed in edible or smoked form.

The term "cannabis extract" is created by processing raw cannabis flower, cannabis plants, or other cannabis plant parts to extract and concentrate cannabis compounds. It should be noted that some, but not all, methods of processing of cannabis into a cannabis extract change the terpene and cannabinoid profile of the original cannabis, such that the cannabis extract has a slightly altered cannabis profile. Ther term "cannabis extract" is used interchangeable with "extract" herein.

The term "cannabis products" means cannabis in any known form including but not limited to cannabis plant matter, cannabis extract, raw cannabis flower, cannabis edibles, cannabis oils, cannabis tinctures, cannabis e-cigarettes, and cannabis cigarettes. The term "cannabis products" is used interchangeably with "products" or "product" herein.

The term "cannabis profile" means the ratio by weight of cannabinoids and/or terpenes in cannabis plants, plant parts, extracts or compositions.

The term "cannabis compounds" shall mean cannabinoids, terpenes or a mixture thereof.

The terms "cannabinoids" and "terpenes" include all known and unknown isomers, stereoisomers, diastereomers, and enantiomers of each, including those that are synthetic manufactured or naturally occurring in cannabis plants or plant parts.

The term "cannabis product data" refers to information input into a recommendation system that may include any descriptive or quantifiable information about a cannabis product including but not form, strain, cannabinoid profile, taste, smell or organoleptic feel. Cannabis product data may also include efficacy data, any treatments or uses for medical, phycological, mental, or otherwise as well as, any known side effects or caveats (medical, phycological, mental, or otherwise) associated with its use. The term "cannabis product data" is used interchangeably with "product data."

The term "cannabis product profile" refers to information generated by a recommendation system that may include any descriptive or quantifiable information about a cannabis product including but not form, strain, cannabinoid profile, taste, smell or organoleptic feel. Cannabis product data may also include efficacy data, any treatments or uses for medical, phycological, mental, or otherwise as well as, any known side effects or caveats (medical, phycological, mental, or otherwise) associated with its use. The term "cannabis product profile" is used interchangeably with "product profile."

A "patient" or "user" is a subject to consume or be treated with the recommendation systems, extracts and/or methods described herein and may mean either a human or non-human animal, such as primates, mammals, and vertebrates. Patient and user are used interchangeably herein.

A "medical professional" is a doctor, nurse practitioner, nurse or other healthcare professional authorized to make recommendations to patients, evaluate patients, and/or access patient records.

The term "patient diagnostic data" includes any information associated with patient health records (medical history, medical conditions, phycological conditions, psychiatric conditions, diseases, symptoms, treatments, medications, side effects, or any other typical information shared with a health care provider) and/or patient cannabis preferences and/or reactions to different types of cannabis, cannabis strains, cannabis profiles, cannabinoids or terpenes. "Patient diagnostic data" is used interchangeably with "diagnostic data" herein.

The term "cannabis provider" is any person or entity that provides or recommends cannabis to users.

A physician, nurse or other medical professional may use software to input patient diagnostic data into a program that may subsequently access stored data specific and defining to available cannabis extracts, wherein the most appropriate extract or extracts for treating the patient's medical condition may be returned as displayed search or match results that might be considered by the physician, nurse or other medical professional in the process of recommending and potentially prescribing a recommended extract to the patient. It has occurred to the inventor that a software program used by the physician, nurse or other medical professional to enter diagnostic information defining a patient's condition could generate an executable object file that includes the diagnostic data, the file download able to a patient's communications or computing device.

FIG. 1 illustrates a method for a medical cannabis recommendation, wherein that a medical professional 3 may evaluate a user 2 and then consult with said medical professional 3 in cannabis products, such as one or more extracts 5 to obtain a recommendation relative to which product or products would be appropriate to prescribe to user 2.

Figure 2:
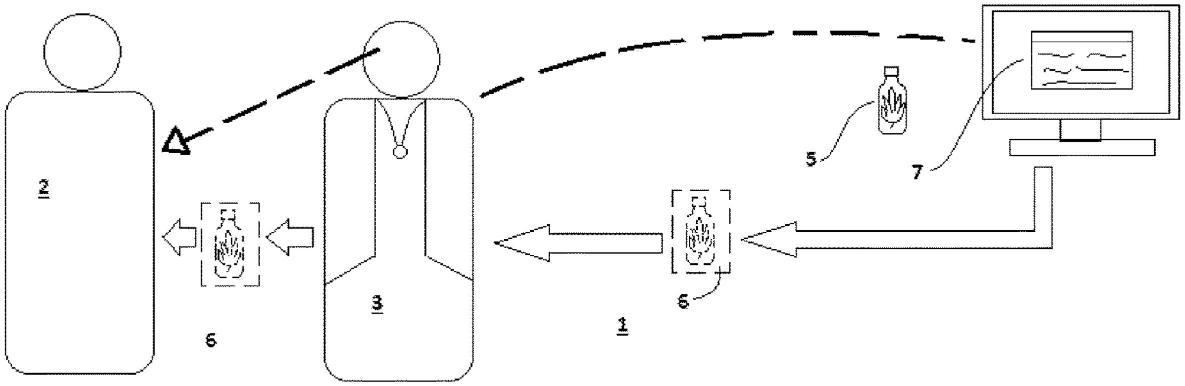
FIG. 2 is a block diagram depicting an alternate method of medical cannabis recommendation.

FIG. 2 illustrates an alternate method for a medical cannabis recommendation that shows a variation of process of FIG. 1, wherein the medical professional 3 may instead enter the diagnostic data into a software program (SW) 7 on a computing terminal, wherein the SW 7 provides a recommendation by matching diagnostic information to knowledge about one or more extracts 5 stored as accessible information in a database to obtain a system recommendation of cannabis products, such as one or more extracts 5 that could be prescribed to user 2. The recommendation is optionally reviewed by a qualified medical health care provider, such as a physician.

Figure 3:
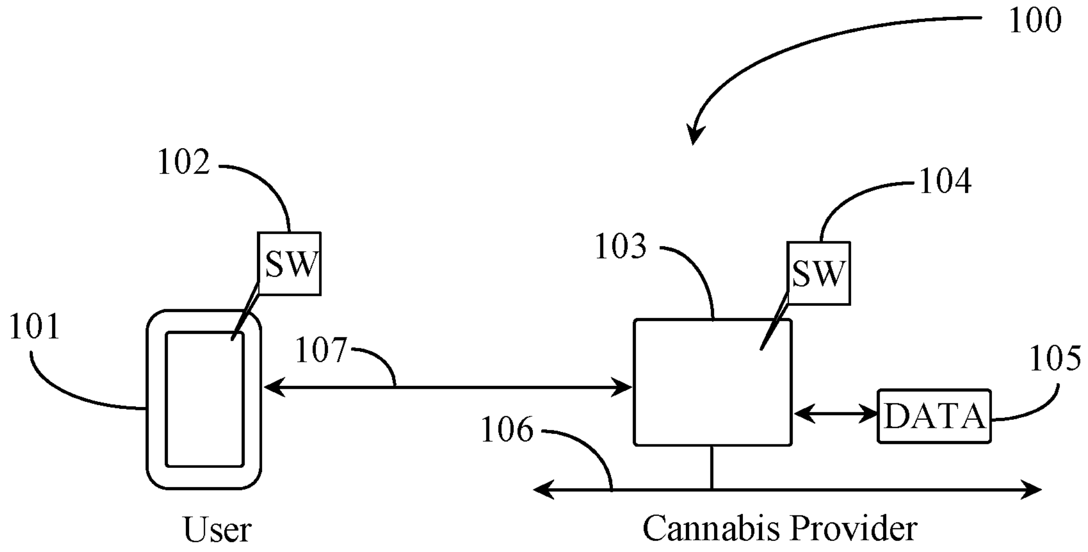
FIG. 3 is a block diagram of a transaction scenario 100 involving a user who is a patient and a transaction terminal of a cannabis provider.

FIG. 3 is a block diagram of a transaction scenario 100 involving a user and a transaction terminal of a cannabis provider. In FIG. 3, transaction scenario 100 may occur between a patient 101, referred to herein as a user 101, and a computing transaction terminal 103 having connection to a local area network (LAN) and at least one data repository 105. User 101 may operate a smart phone or other hand-held computing device capable of wireless file transfer with a compatible device such as transaction terminal 103.

A software client 102 may be provided to the device of user 101 by a medical professional who previously consulted with or treated user 101 as a patient and entered diagnostic data into a resident software program provided on a terminal accessible to that medical professional. The medical professional may prompt the user to download an executable file represented herein by SW 102 after diagnosis and diagnostic data entry into the parent SW program depicted in FIG. 2 as SW 7. It is assumed herein that SW 102 is an electronic file that is executable to present entered diagnostic data and is transferable to another device such as transaction terminal 103 hosting a software program 104.

Diagnostic data may include but is not limited to medical condition type and stage whether a condition is physical, phycological or mental, or a combination thereof, symptoms of the condition, medications and regimens being used already to treat the condition, side effects exhibited to any existing medications, and so on. File 102 may be stored on the device of user 101 in an encrypted format for privacy purposes. In one embodiment, user 101 may decrypt the diagnostic information to read the information. In a variation of this embodiment, user 101 may be an agent working on behalf of the patient defined by file 102, such as a nurse, caretaker, or relative authorized by the patient, etc.

SW 104 on transaction terminal 103 is adapted to receive a copy of file 102 from the device of user 101 over a wireless data link 107. Data link 107 may be any type of wireless link protocol, known or unknown, including but not limited to Bluetooth™, Wireless Fidelity (WIFI), wireless universal serial bus (USB) or near field communication (NFC). In one embodiment, user 101 may present the communications device with file transfer on to the transaction terminal 103 to pass the file to SW 104. File 103 may be encrypted during the transfer and may remain machine readable but not human readable once on terminal 103. SW 104 may parse file 103 for diagnostic information about user 101 and may use the data to perform a data search for product information contained in data repository 105 that best fits the diagnostic data in file 103 relative to efficacy of the product relative to treating symptoms of the user according to the diagnostic file 103.

Data in repository 105 may be compiled over time by entering descriptive cannabis product data into SW 105 wherein SW 104 may generate a product profile for a product that is available to user 101 at the outlet or pharmacy. For a cannabis outlet, there may be hundreds of cannabis products available to cannabis users where the individual products may vary in form, strain, and cannabinoid profile. Data repository 105 may contain additional information about general efficacy of product profile attributes in treating certain symptoms that are brought on by certain medical conditions and or drugs used to treat conditions. These data may be appended to product profiles as granular attributes of the product model for a specific product. For example, a cannabis extract with a high level of cannabidiol (CBD) may reference efficacy for treating pain and inflammation, caused by several medical conditions. Similarly, a product with a high level of tetrahydrocannabinol (THC) may reference efficacy for treating any number of conditions or symptoms, including but not limited to nausea caused by some medical treatments like chemotherapy, anxiety caused by a mental condition, etc.

SW 104 provides a list of recommended cannabis products to display on a display screen of the transaction terminal 103 for either a worker operating the terminal to see or directly to the user to see, wherein the transaction terminal is automated and operated like a kiosk transactional terminal. If transaction terminal 103 is attended by a worker, that worker may not be authorized to know the medical condition of the patient due to encryption of the diagnostic data transferred from the user device. However, the worker may receive a display listing the top two or three recommended products for the patient according to the mapping process just performed. In this case a second professional is not required to provide a recommendation based on personal experience. Efficacy data may be added to product profile attributes or associated instead with specific CBD compounds.

Efficacy data entered into repository 105 may be vetted by one or more professionals and may be backed by current research and empirical results of testing including consensus figures from multiple polled or interviewed or evaluated patients and/or users that received the product and testified to symptom alleviation. Object modeling may be used to create the patient medical profile and the product profiles wherein the SW 104 retrieves product profiles that best answer the requirements of the patient's profile. The user 101 may obtain an updated medical profile from a medical professional as a condition worsens or gets better, or new symptoms arise. Medical profile updating may be required periodically such as every three months, for example. Therefore, as a user's medical profile evolves, the list of products returned for recommended use will also evolve.

The inventor provides at least one process for extracting essential or desired cannabis compounds from a raw organic cannabis plant matter and preserving those compounds in an extract, oil or paste that is used to create many products that might be purchased at a cannabis provider location or outlet. Raw cannabis plant matter used to create pure extracts, oils or pastes, may differ greatly in their cannabinoid and terpene profiles. All such raw cannabis plant matter typically has a grade or certification that tells the manufacturer what strain, variety, and traceable cannabinoids and terpenes are present in the raw cannabis plant matter.

The inventor has refined one or more extraction processes that provide unexpected results, by employing unique process variations adapted to preserve compounds that may be present in raw cannabis plant matter. More detail about the extraction process is provided later in this specification. Extracts, oils, or paste created in the described process may vary in which specific essential cannabis compounds were intentionally preserved. Each of these extracts may be profiled using the original certification data of the raw cannabis plant matter processed and data obtained from fresh testing of the output product for detectable CBD compounds preserved in process. Therefore, a product profile may be created that is unique to each produced extract, oil, or paste to create a product profile for the final extract, oil, or paste. The final extract, oil or paste may be further incorporated into a different form of cannabis product There are approximately 113 different kinds of cannabinoids that may be present in a cannabis plant. As new research may discover new efficacy data for certain detected CBD compounds, stains may be engineered to elevate the typical percentage of that CBD compound in a raw plant that might be processed. Likewise process variants in isolation of cannabis compounds may be utilized to tailor the profile even further. In the process referenced herein, the inventor provides optimized product profiles by selective mixing of final extracts, oils, or paste to produce a product profile sharing CBD attributes of both starting extracts, oils or paste.

Figure 4:
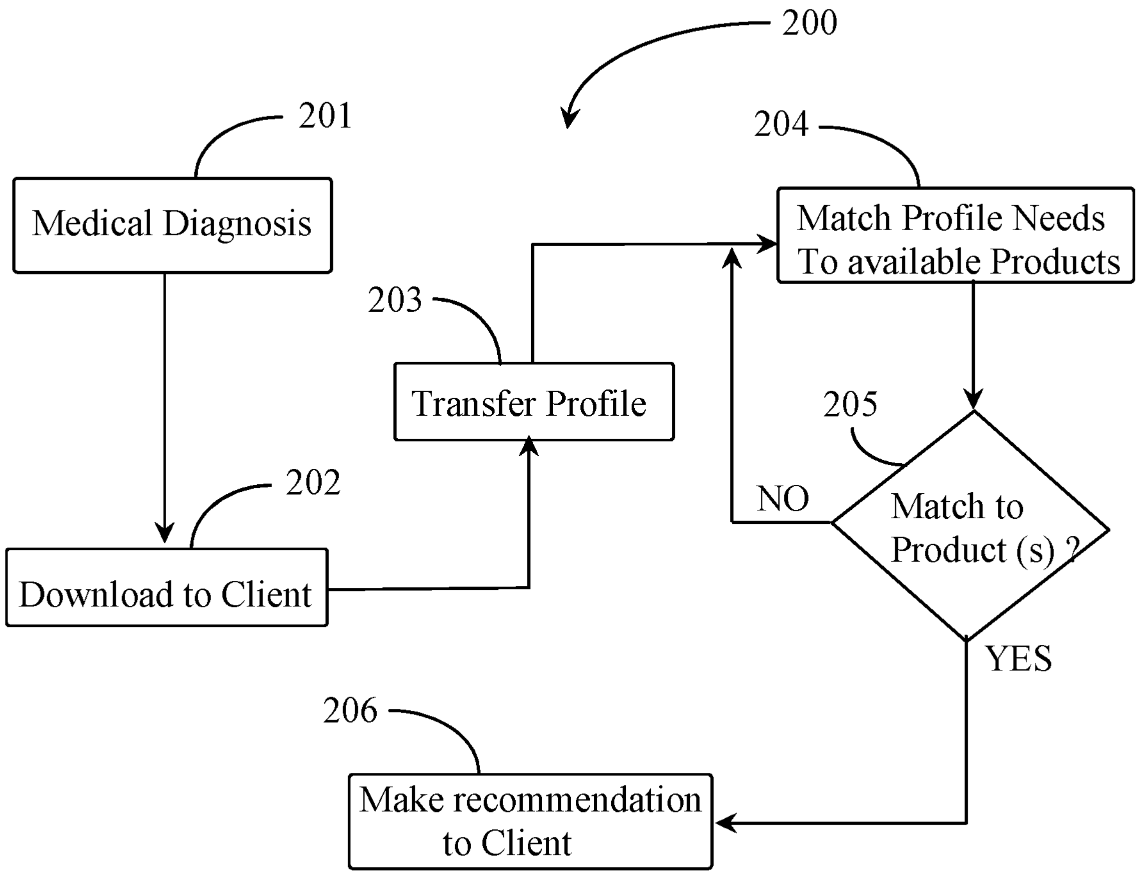
FIG. 4 is a process flow chart depicting steps for creating an electronic file containing a patient medical profile based on a patient diagnosis and transferring that file to a software aided computerized system for matching the profile to one or more available product profiles for recommendation to the patient.

FIG. 4 is a process flow chart 200 depicting steps for creating a patient medical profile and using the profile to search for top matching cannabis product profiles. At step 201, a user having one or more diagnosable conditions may obtain a medical diagnosis and evaluation from at least one medical professional at step 201. It may be that the client has two or more conditions wherein each condition is monitored by a different medical professional. If so, then all the data is aggregated to one location. At step 202 the medical diagnostic model representing the patient's medical profile may be downloaded onto the patient's electronic device, such a computer, smart phone or tablet. The data may be downloaded in an encrypted format that is machine readable but not human readable. In one embodiment, the diagnostic data is a digitally coded executable patient state diagnosis object model. The data may be downloaded in an encrypted format that is machine readable but not human readable.

The patient may decrypt the diagnostic data to render it readable and may authorize others to possess and decrypt the data. In one embodiment, a healthcare worker, relative of a patient or other authorized person is the user that may carry the downloaded patient medical profile. In one embodiment, a patient may download a medical profile from a website server upon secure notification to the patient that the profile is available for download. In this variant embodiment, the relative, healthcare worker or other authorized person may enter into a transaction as described in FIG. 3 above on behalf of the patient who may be unable to travel.

At step 203, a user may travel to a cannabis product outlet, a collective, or a pharmacy that provides cannabis medical products and initiate a transfer of his or her encrypted medical profile into a transaction terminal using short wave or other wireless protocol. The terminal may be a manned or attended terminal or an automated kiosk type terminal that is unattended. On the terminal at step 204, the system matches the medical profile needs parsed from the received medical profile model to stored product data models representing product profiles of available products stored for access in a data repository accessible to the terminal or a first server such as on a LAN network or on the larger Internet network and accessible through the LAN network, for example.

At step 205, the system decides whether a match was made to any product data models. An algorithm or a set of algorithms may be provided to map medical condition and symptom meta data to product efficacy meta data associated directly or indirectly to product data models as attributes of objects. If at step 205 there are no matches the process may loop back to step 204 until a best match is found. In one embodiment, a patient may set a parameter for recommendation of products such as the top five products available. The algorithm may be a search algorithm in one embodiment. In another embodiment, the algorithm may consult a separate knowledge base dedicated to efficacy data associated with specific CBD compounds, and then uses that information to select the best products from multiple available products. In one embodiment a tagging system may be utilized wherein parse able tags are attributed to meta data about products. In this embodiment the tags weigh efficacy in treatment of or at least compatibility to of one or more medical conditions and or symptoms derived from the patient state diagnostic model.

If the system determines that a match to one or more product profiles was made, the process may move to step 206. In step 206, the system makes the recommendation directly or indirectly to the client, which is the user. In one embodiment, the recommended products are listed in order of efficacy on a display on the transaction terminal complete with pricing information. An attendant may then gather the products and present those products to the user or a medical professional for consideration. If there is no attendant and the transaction terminal is a kiosk operated by the user, then the display will be to the user who may then receive a notification from the terminal listing the products and product pricing. At times the attendant may be a pharmacist. For instance, in a pharmacy, the pharmacist would serve as the attendant. In an alternative embodiment a display may be sent directly to the patient's communications device for display allowing the patient to receive the information independently of the attendant. In this way the patient may narrow their choice and know pricing and use while the attendant is with someone else saving time in product selection and in transacting. In still another embodiment, the system may include a feedback mechanism where current products being used are added to the medical diagnostic data as treatments, for example CBD extract and doses taken regularly. Later the patient gets a new evaluation or update and the new medical diagnostic file may include changes in condition state and symptom presence or frequency. The system may determine whether to change a recommendation for a cannabis product for example under current use based on the new data. It may help the system validate, verify, confirm, or question efficacy of a certain product for that patient. General tags for a cannabis product or compound may also be revisited and changed based on new data received over several random patients.

Figure 5:
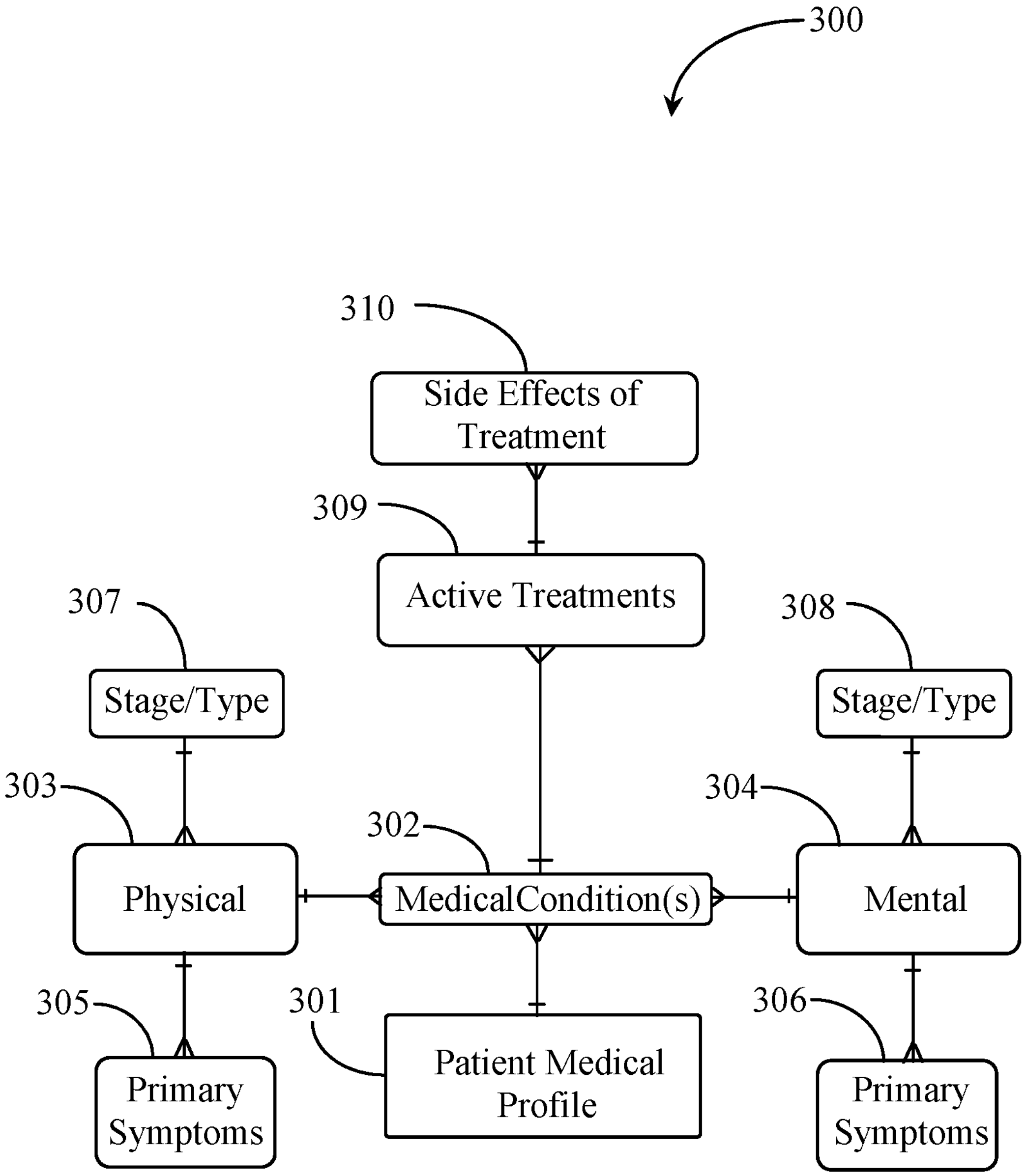
FIG. 5 is a UML diagram representing a generic object model of a patient medical profile.

FIG. 5 is a unified model language (UML) diagram depicting an object model 300 representing a patient medical profile. In one embodiment of the present invention object modeling language may be used to create a generic patient medical profile template that may be data filled by a diagnosing medical professional. In one embodiment, a patient medical profile will be contributed to by more than one medical professional in the case of more than one condition afflicting the patient. Object model 300 is generic for a patient medical profile 301 (parent object). Profile 301 has one or more than one medical condition 302. A medical condition could be defined as any condition requiring any sort of medical, physiological or phycological attention. The one or more medical condition may include a psychological or mental condition 304 including but not limited to anxiety, depression, sleeplessness, personality disorder, or any other known condition for example. The one or more medical conditions may include a physical condition 303, including but not limited to a heart condition, cancer arthritis, epilepsy, chronic pain, arthritis, and so on.

Object model 300 includes sub-attributes associated to both attributes physical condition and mental condition for each condition diagnosed. For example, a mental or phsychological condition 304 may include a stage and a type sub-attribute 308 (if more than one type) of the condition for each condition. Further sub-attributes may include primary symptoms 306 that are exhibited by the patient. The attribute physical condition 303 has sub-attribute stage/type 307. For example, if the physical condition is cancer and the sub-attribute 307 is stage IV melanoma. Primary symptoms then could include pain, neurological symptoms (stage IV brain tumor), and other symptoms relative to mobility, etc. Each generic model becomes a unique object model for a patient medical profile.

Object model 300 includes the attribute active treatments 309. Active treatments may be defined as any medical treatments rendered professionally to a patient such as medications taken, physical therapies taken, infusions received, psychological medications taken. Active treatment attribute 309 may include sub-attributes 310 listing any side effects for each listed treatment. For example, if the active treatment is chemotherapy for melanoma then the side effects of treatment may include fatigue, nausea, and loss of appetite. Therefore, the SW algorithm that matches product profiles to patient medical profiles may be refined to consider the attributes and sub-attributes like side effects of treatment and treatment modality in addition to primary symptoms alone. This granularity allows more safety for patients who may not otherwise be able to successfully self-regulate cannabis type medications.

Figure 6:
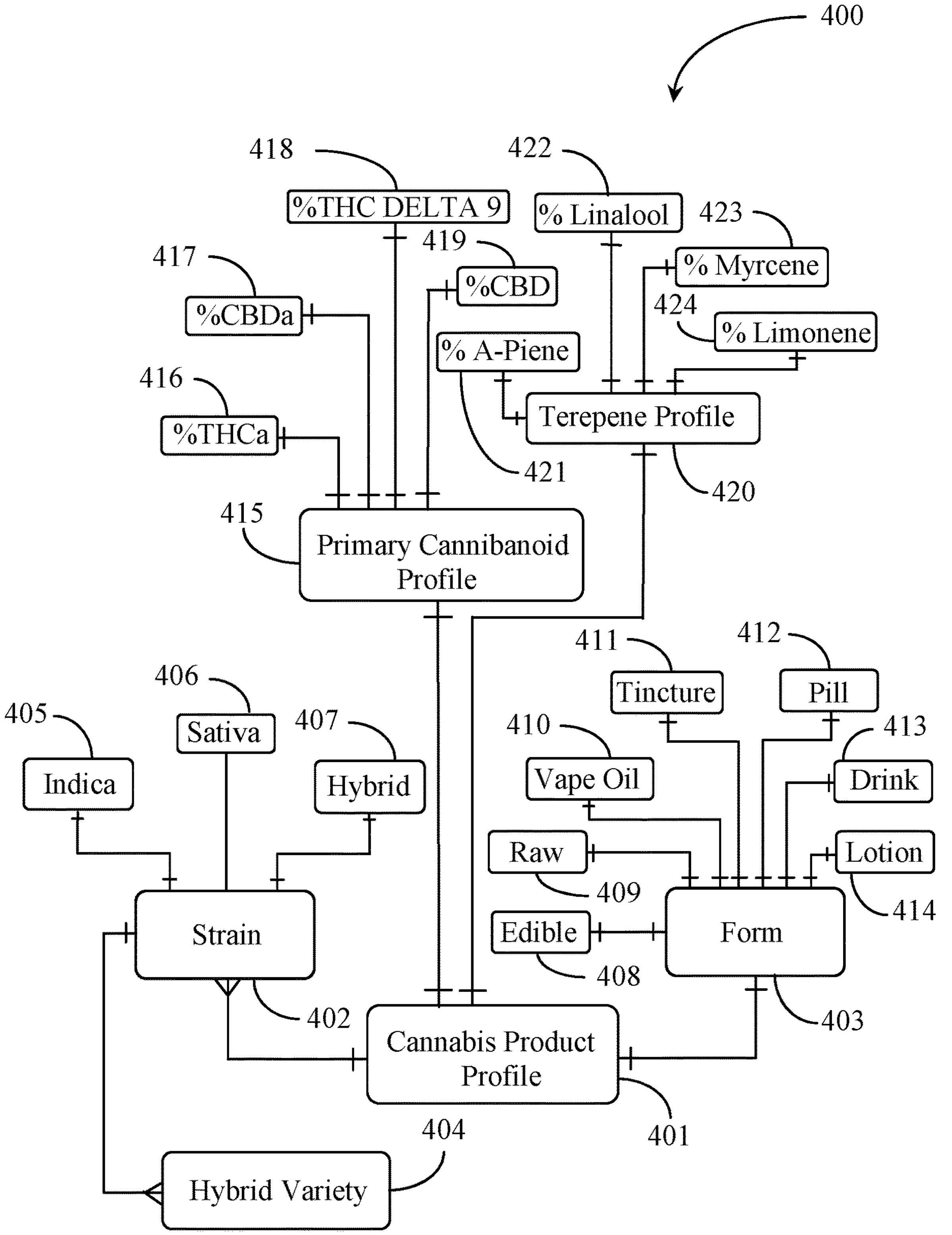
FIG. 6 is a UML diagram representing a generic object model of a cannabis product profile.

FIG. 6 is a UML diagram depicting an object model 400 representing an exemplary cannabis product profile according to an embodiment of the invention. Object model 400 is a generic model that may be data filled by an authorized professional that has access to documented information about the product. A product profile may be created for each product that is available to consumers through the provider.

Object model 400 includes a parent node cannabis product profile 401. Cannabis product profile 401 includes an attribute 402 strain. The strain of the cannabis is known before a product may be completely formed. Strain attribute 402 may be an Indica strain, sub attribute 405, a sativa strain, sub attribute 406, or a hybrid of each, sub attribute 407. The strain of the product may be considered when matching the product to a patient medical profile.

Cannabis product profile 401 has a form 403. Form attribute 403 simply identifies the form of the available product. Form 403 may be one of edible form 408, a raw smokeable product 409, a vape oil 410, a tincture or extract 411, a pill 412, a drink 413 or a lotion 414. The form of the product may be considered relative to a patient medical profile before matching the product profile to the medical profile. For example, if a medical patient has COPD, then the candidate forms available may exclude raw cannabis 409 or vape oil 410 for the safety of the user. If the patient has diabetes, the form considered may be narrowed by algorithm to forms not containing high amounts of sugar. If a primary medical condition is rheumatoid arthritis, then a recommended cannabis product 401 included in a returned list of products may be in the form of a lotion 414.

Cannabis product profile 401 has a primary cannabinoid profile 415. Cannabinoid profile 415 is an aggregation of all the detected cannabinoids and the percentage of those by volume in the product. Though there are 113 different cannabinoids so far know to be present in cannabis, typically the primary cannabinoids having more volume and medical efficacy are sought for preservation in any manufacturing process. The primary cannabinoid profile 415 may have a percentage of THCa 416, a percentage of CBDa 417, a percentage of THC, and a percentage of CBD 419. Other known cannabinoids may be added to the list if detected in a strain of cannabis and if efficacy characteristics of the cannabinoid warrant including into the model.

Cannabis product profile 401 also has a terpene profile 420. A terpene is an aromatic compound found in the resins of many plants. Cannabis includes a variety of terpenes that can be lost during manufacturing or processing of the raw plant. Terpenes comprise the smell or aroma of the plant and can make up 30% of the active compounds including cannabinoids. Unlike terpenes, cannabinoids do not have any aromatic properties. Over 100 different terpenes have been detected in cannabis plants. Like the cannabinoids, there are typically primary terpenes or those most often detected in larger volume.

Terpene profile 420 may include a percentage of A-Pinene 421, a percentage of linalool 422, a percentage of myrcene 423, and a percentage of limonene 424. Terpenes such as these have been evaluated for efficacy in treating some symptoms in general such as reducing inflammation, promoting antiseptic activity, increasing circulatory capacity, reducing gastric acid, and so on. Therefore, the algorithm matching a product profile to a patient's medical profile may further consider the terpenes and the efficacy attributed to them to treat patient symptoms. Efficacy data attributed to terpenes and cannabinoids may be backed by empirical testing, patient consensus, and through published research. The algorithym may also consider other attributes such as taste, smell and organoleptic feel.

Figure 7:
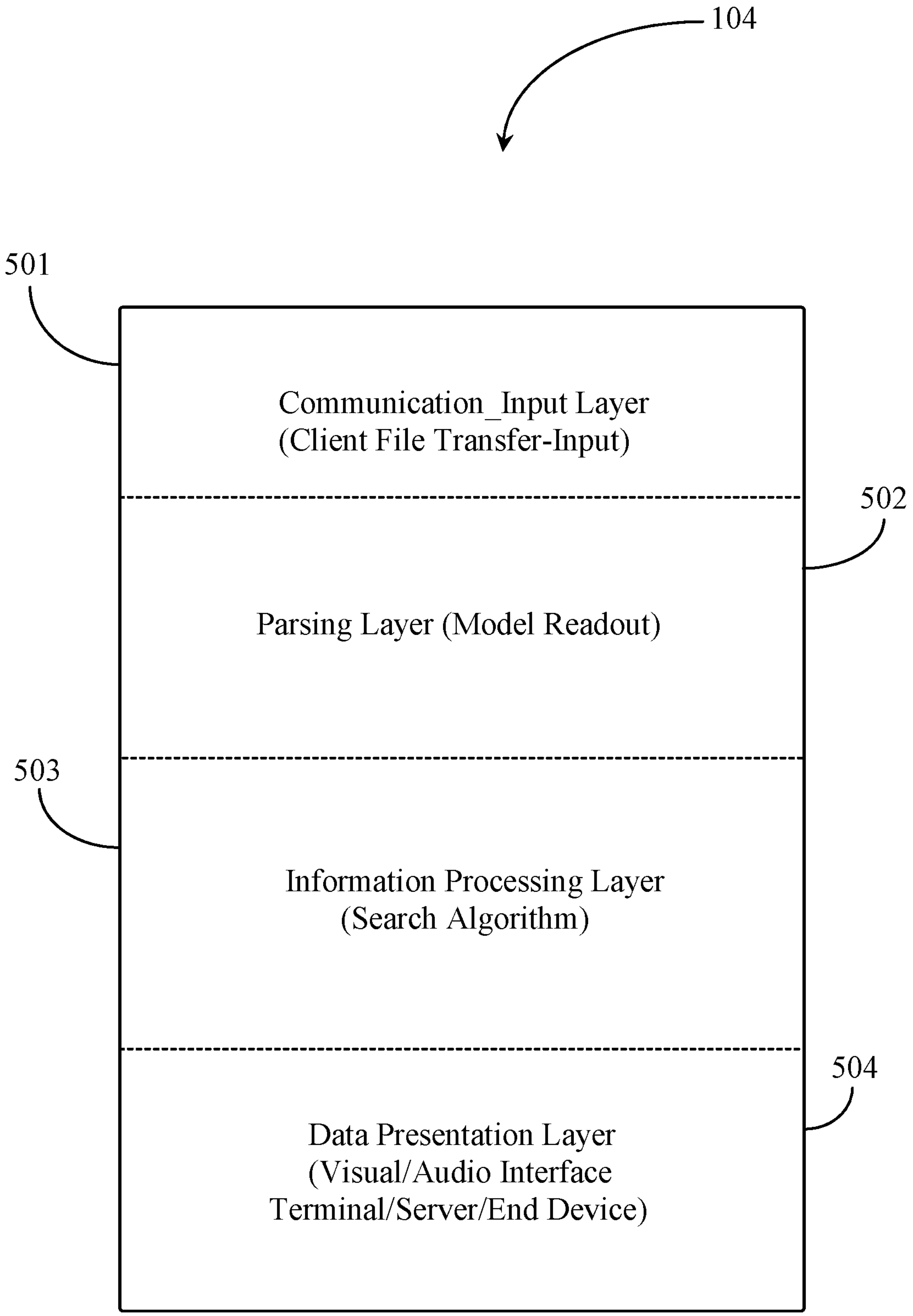
FIG. 7 is a block diagram depicting software for matching a patient medical profile to one or more cannabis product profiles.

FIG. 7 is a block diagram depicting functional software layers of the terminal software 104 of FIG. 3. SW 104 includes a communication and input layer 501 adapted to recognize a client file representing the client medical profile and accept it from the client device over a wireless link. A wired link may also be used in some cases to transfer the file or it may be transferred remotely over a network to the transaction terminal without departing from the spirit and scope of the invention. For example, a patient may be immobile and have cannabis products delivered. In such a scenario, the patient my contact the provider's website and access the terminal, select a system recommended product and finish the transaction over the network. However, in a preferred embodiment an attendant may provide final advice to a patient who has selected one of more than one recommended product for purchase. This is similar to obtaining advice from a pharmacist when purchasing a prescribed medication.

SW 104 includes a parsing layer 502 adapted to execute (expand) the file and to access the data and parse out the patient medical data during product data selection. SW 104 may include an information processing layer including one or more algorithms for searching in a product profile database for the available products that will best serve the patient's medical conditions and or symptoms. The actual mapping process may be a combination of search and comparison analysis where product attributes may be compared to each other before being selected to include in a list of returned product profiles. The returned product profiles may include pricing and availability, dose recommendation, and similar descriptive data. A tag system might be utilized to tag a product attribute as either good, or poor, or neutral in that attribute having efficacy in treatment of the condition or symptom. An attribute of a product may be associated with many tags reflecting good, poor, or neutral for relative number of potential conditions and symptoms known in patients.

It is important to note herein that from a raw extract, paste, or oil, other processes may be performed to create some variant forms of product such as edibles, drinks, and tinctures. Such processes may result in loss of terpenes and or cannabinoids listed in the extract. In that light, some cannabis forms may require retesting for cannabinoids and terpenes to determine efficacy. Whether or not the variant form cannabis had been tested or the results of testing these variants, would be included or incorporated in the data.

SW 104 includes a data presentation layer 504. Data presentation layer 504 is adapted to display a list of product profiles wherein each entry may be an executable file one may manipulate to expand to display various aspects of the profile including the efficacy data, the pricing and availability data, and any other information the provider wishes to include such as hybrid history of a base strain used to make a product and so on. An attendant for a cannabis provider may work the transaction terminal and may be able to manipulate the returned list by asking for more entries or less entries.

Many growers are breeding strains that are valuable medically as the market for medical cannabis grows. Some hybrids have been in refinement and use for 20 years or more at the time of this writing and are specifically recommended to cancer patients or epilepsy patients. Manufacturers making extracts may have knowledge of certification of specific compounds in a raw cannabis plant matter and may select the desired raw cannabis plant matter accordingly for processing. Furthermore, the manufacture may vary a process with steps that may alter the overall cannabinoid profile of the raw cannabis plant matter. Extracts having certified test results can be selected to be mixed together to produce a compound that includes the best compounds of both the original extracts.

The inventor also provides at least one unique and flexible manufacturing process that produces raw cannabis extract, oil, or paste from raw cannabis plant matter, typically the flowers and leaves of the cannabis plant. Unique efficacy characteristics for treatment of certain medical symptoms may be managed somewhat at the growing and processing level. The inventor provides at least one refined manufacturing process described in detail in the following examples.

Processing

In a preferred embodiment, a process is provided of extracting cannabinoids and terpenes from raw cannabis plant matter to substantially preserve the original cannabinoid profile including terpenes of the raw cannabis plant matter.

In one embodiment of the invention, terpenes are sought for preservation along with primary and secondary cannabinoids that might be represented in a cannabinoid profile of a raw cannabis plant material selected for processing. In one embodiment, special cannabis strains may be selected and processed to recover target compounds for preservation wherein more than one selected strain may be mixed together after individual processing in recommended ratios to create a medicinal compound for a patient that presented a medical profile where the targeted compounds sought for preservation are known to be beneficial to that patient. This may happen for example, if the provider could not provide more than a moderately beneficial product to a patient prompting the patient to order special processing.

Figure 8:
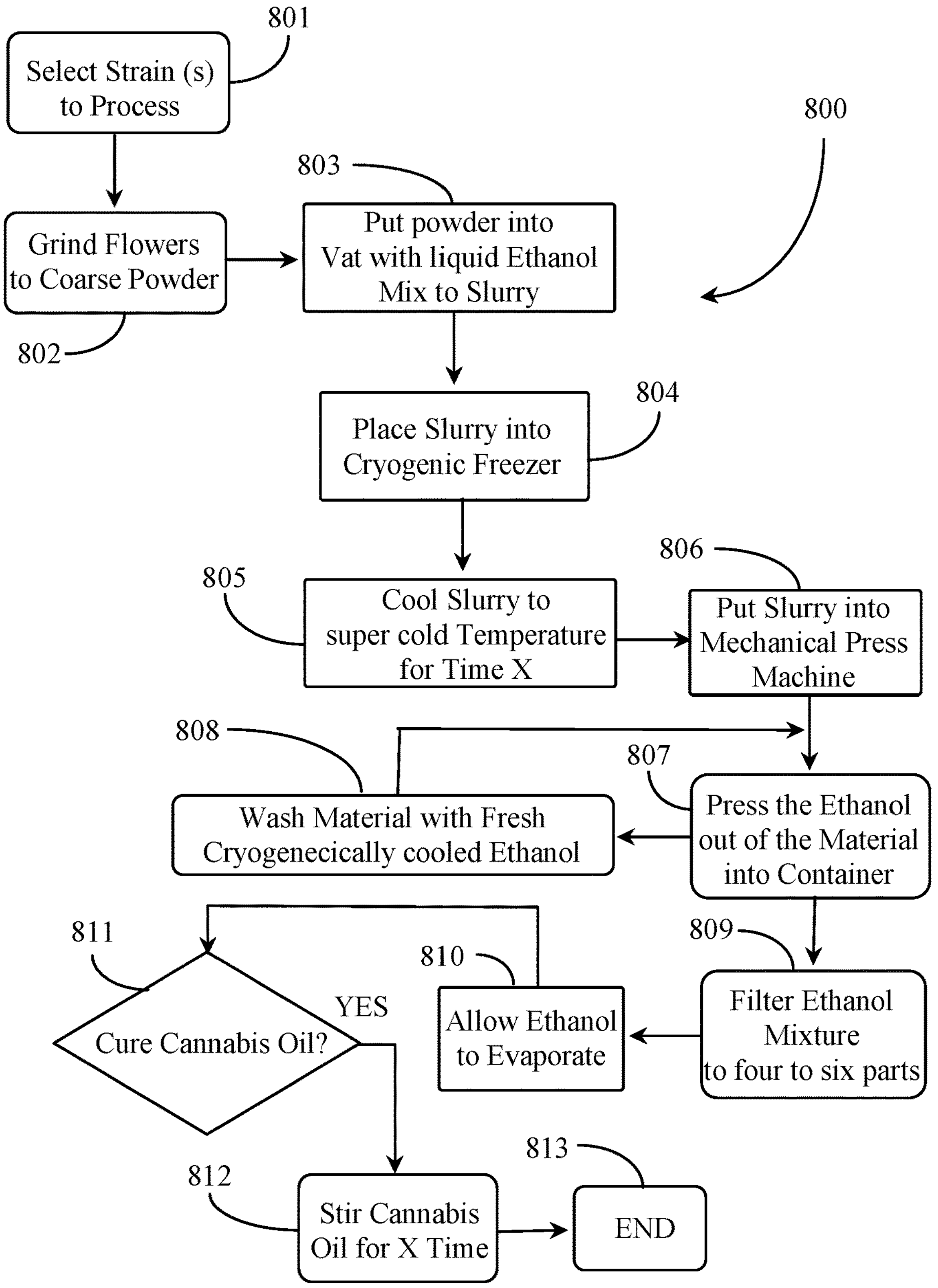
FIG. 8 is a process flow chart illustrating a process for extracting cannabinoids and terpenes from a raw cannabis plant matter.

FIG. 8 is a process flow chart 800 depicting process steps for extracting cannabinoids and terpenes from a raw cannabis plant matter. In step 801, a manufacturer or user may select an appropriate amount of dried cannabis flower having a targeted or otherwise desired cannabinoid/terpene profile. For the purposes of discussion assume 1 pound (lb) of cannabis flower is selected. The cannabis selected will have a strain or hybrid profile and will have documentation as to cannabinoid profile including a terpene profile that may be compiled separately from a primary cannabinoid profile.

At step 802, the dried cannabis flower is placed in a grinding machine and ground down to a coarse powder. It is noted herein that if more than one raw cannabis is desired or selected to be processed, then the correct portions of each product up to a pound, in this example, are aggregated into one batch for processing. In another embodiment, each raw cannabis strain or hybrid may be processed separately wherein the final compounds may be blended according to a previously designed ratio of one compound to another to form a single medicinal compound such as an oil, extract or paste.

At step 803, the aggregated cannabis coarse powder may be placed in a container with approximately one gallon (based on weight of input cannabis powder) of liquid ethanol and thoroughly mixed to form a cannabis slurry. Mixing may be by an automated drum or other mechanical implement with access to the slurry. Once the slurry is ready to be cooled at step 804, the cannabis slurry is placed into a cryogenic freezer and is supercooled, at step 805, down to approximately −170 Fahrenheit and the ethanol is at a super cold liquid state. In this step the slurry is kept in the cryogenic freezer for approximately 48 hours at the maintained temperature.

At step 806 the slurry may be removed from the cryogenic freezer and placed in a mechanical press container with suitable capacity for holding the displaced liquid. At step 807, the ethanol is pressed out of the cannabis powder by the mechanical press and collected. The ethanol solution contains the target cannabinoids and terpenes listed in the raw cannabis certificates. In step 808, the expunged cannabis grinds are washed with approximately one quart of fresh supercooled (approximately −170 F) ethanol from the cryogenic freezer. This process may take place in a same mechanical press container holding the original ethanol/cannabinoid solution. In another embodiment, separate containers might be employed. Back at step 807, the ethanol wash is pressed out of the cannabis grounds. Steps 808 and 807 may be repeated as desired, typically three or four times until it is determined the cannabis grounds have been stripped of cannabinoids and terpenes.

At step 809, the ethanol wash and the original solution are filtered into four-to-six divisional parts for evaporation. In one embodiment, coffee filters or fabric or paper filters might be used with micron ratings of approximately X microns. At step 810, the filtered ethanol solution is evaporated at approximately 173 F resulting in a thick cannabis oil containing the cannabinoids and terpenes desired from the original raw cannabinoid/terpene profile.

The oil produced weighs approximately 600 to 700 milligrams (mg) based on the weight of the raw material input into the process. In one embodiment, at step 811, a determination might be made by the processing user whether to cure the cannabis oil. If at step 811 the user determines to cure the cannabis oil produced by the above described process, then at step 812 the cannabis oil may be heated to a desired temperature, for example 173 F and stirred continually for approximately no less than 6 hours but not more than 36 hours. Curing may result in a thicker residue like a wax. The process may end then at step 813. If at step 811, it is determined no curing is necessary, then the process may move to step 813 and end bypassing the optional curing process. It may be noted herein that heating the cannabis oil in the process of curing may affect the final cannabinoid profile relative to some primary cannabinoids and terpenes.

Likewise, the maintained temperatures of the cryogenically cooled ethanol slurry function to preserve delicate compounds and separate those compounds from the undesired plant matter that is later filtered off.

In one aspect of this process another optional preparation step for a final product may be to oven dry the cannabis residue created by step 812 in a vacuum oven for an approximate time 12-36 at a sustained approximate temperature of 99-170 F. The final product may also be tested to ensure compliance with local standards. A final compound may weigh in at approximately 80 mg to 100 mg per pound. The final product tests to be substantially pure containing the desired or targeted cannabinoid and terpene profiles from the raw cannabis for medicinal treatment of symptoms of conditions suffered by patients who may need relief.

The process aspect of the invention provides a surprisingly clean cannabis extract that substantially retains the cannabinoid profile of the original cannabis plant. This can be further altered to treat general symptoms of medical and/or psychological conditions such as cancer, cancer treatments, anxiety, epilepsy, eating disorders, drug addiction. General symptoms may include pain episodes, nausea, congestion, hypertension, restless leg, anxiety, irritability, cramping, or involuntary twitches or seizures.

One way the inventor has been able to tailor the cannabis extracts herein, are by varying the temperature level for curing based upon the type of cannabis, and the cannabis compounds that meet needs of a patient.

Specifically, the inventor has discovered that patients seeking treatment for pain use a profile of FIG. 7. This is achieved by the processes described herein, wherein the cannabis is cured at 99 to 170 F temperate for 6 to 36 hours, which provides variable results, wherein each result may have a different or desired effect.

It will be apparent to one with skill in the art that the cannabis extraction and cannabis product recommendation system of the invention may be provided using some or all the mentioned features and components without departing from the spirit and scope of the present invention. It will also be apparent to the skilled artisan that the embodiments described above are specific examples of a single broader invention that may have greater scope than any of the singular descriptions taught. There may be many alterations made in the descriptions without departing from the spirit and scope of the present invention. The present invention shall only be limited by the following claims.

What is claimed is:

1. A network hosted product selection system configured to select a cannabis product for a patient, the network hosted product selection system comprising:

a first server on the network, the first server having at least one connected data repository, the first server including a non-transitory medium coupled thereto, the non-transitory medium containing thereon instructions for the server to:

accept a digital file in the form of a digitally coded patient state diagnosis model from at least one of a connected input communications device or memory device, the patient state diagnosis model including an identification of at least one diagnosed condition of the patient;

execute and parse the patient state diagnosis model for information including the identification of the at least one diagnosed condition of the patient;

compare parsed information with information derived from individual ones of product data models, the product data models including parse-able tags weighing product efficacy in treatment of the at least one diagnosed condition of the patient;

determine a first percentage of a first cannabinoid and a second percentage of a second cannabinoid;

select one or more than one of the product data models from the at least one connected data repository based on at least collective tag weight resulting from comparison as preferred products for patient use, and the first percentage of the first cannabinoid or the second percentage of the second cannabinoid in conjunction with the at least one diagnosed condition of the patient;

present a human-readable display listing the preferred products and associated transactional data and product use recommendation data;

receive, via a feedback mechanism, a patient input corresponding to the product use recommendation data and patient use data associated with use of a particular product of the preferred products, wherein the patient input is required prior to obtaining a new product from the preferred products and the patient input is associated with an effectiveness of the particular product relative to the at least one diagnosed condition of the patient;

determine, based on the patient input, the patient use data, and the first percentage of the first cannabinoid or the second percentage of the second cannabinoid, a modification to the data product model, wherein the modification comprises re-weighting the tags associated with an individual cannabinoid and terpene profile present in the particular product, and the modification contributes to selecting the preferred products from the one or more than one of the product data models;

propagate the re-weighting to other product data models of the one or more product data models that share the cannabinoid and terpene profile to contribute to a subsequent recommendation of the preferred products;

generate an update to a patient profile associated with the patient based on the patient use data; and transmit the modification to the at least one connected data repository.

2. The network hosted product selection system of claim 1, wherein the first server on the network is selected from a group consisting of a transaction terminal in a cannabis dispensary, a pharmacy selling cannabis products, or other business authorized to prescribe or sell cannabis products, and a computer device operated by a cannabis dispensary or pharmacy cannabis dispensary, a pharmacy selling cannabis products, or other business authorized to sell or prescribe cannabis products.

3. The network hosted product selection system of claim 1, wherein the at least one connected data repository includes product data models including parent objects and child objects and attribute objects representing at least product strain, product consumption form, volume and identification of CBD compounds, THC compounds, and Terpenes.

4. The network hosted product selection system of claim 1, wherein the connected communication device is selected from a group consisting of a mobile cellular telephone, a thumb drive, a computer, and tablet.

5. The network hosted product selection system of claim 3, wherein the at least one connected data repository is updated to contain additional information about general efficacy of the profile attributes for cannabis products, and an algorithm or a set of algorithms maps product efficacy in one or more medical conditions or symptoms derived from the patient state diagnosis model.

6. The network hosted product selection system of claim 1, wherein the parsed information from the patient state diagnosis model includes but is not limited to patient diagnosed condition or conditions, symptoms of the condition or conditions the patient is exhibiting, and medications including dose information the patient is taking for the condition or conditions.

7. The network hosted product and selection system of claim 1, wherein the tags are attributed to product data model objects and attributes and are specific to the conditions and symptoms a patient discloses in the patient state diagnosis model.

8. The network hosted product and selection system of claim 7, wherein tags are used after condition and symptoms are parsed to retrieve products that are good for the patient according to the tags, and wherein aggregated knowledge data is used as guideline information to set tag value.

9. The network hosted product and selection system of claim 7, practiced over the larger Internet network, the first server on the Internet and accessible to a transaction terminal on a LAN.

10. The network hosted product selection system of claim 1, wherein products provided to patients to treat medical conditions are added to the patient state diagnosis model as regimens taken to treat said conditions or symptoms and are disclosed by the patient in an updated patient state diagnostic model on a return visit to a dispensary or pharmacy.

11. The network hosted product selection system of claim 10, wherein a product is parsed as a regimen of treatment and other changes in symptoms of one or more of the patient's conditions may be noted as data for resetting tag values for that product.

12. The network hosted product and selection system of claim 1, wherein the patient state diagnosis model is generated as an object model that includes one or more sub attributes that are used to determine the preferred products for patient use.

13. The network hosted product and selection system of claim 12, wherein the one or more sub attributes include at least one of: a physical condition, a mental condition, a stage, a type, or a symptom.

14. The network hosted product and selection system of claim 1, wherein the product use recommendation data includes a dose that is determined based on the patient state diagnosis model.

15. The network hosted product and selection system of claim 1, wherein the one or more product data models are selected based on an identification of a match between any information in the patient state diagnosis model and the one or more product data models.

16. The network hosted product and selection system of claim 15, wherein the one or more than one of the product data models from the connected data repository after no match was found and responsive to no match being found, an iterative search is conducted for a match until a match is found.

17. The network hosted product and selection system of claim 1, wherein the patient state diagnosis model is periodically updated.

18. A method to identify a product for a patient, the method comprising:

receiving a digital file in the form of a digitally coded patient state diagnosis model from at least one of a connected input communications device or memory device, the patient state diagnosis model including an identification of at least one diagnosed condition of the patient;

executing and parsing the patient state diagnosis model for information including the identification of the at least one diagnosed condition of the patient;

comparing parsed information with information derived from individual ones of product data models, the product data models including parse-able tags weighing product efficacy in treatment of the at least one diagnosed condition of the patient;

determining a first percentage of a first cannabinoid and a second percentage of a second cannabinoid;

selecting one or more than one of the product data models from a connected data repository based on at least collective tag weight resulting from comparison as preferred products for patient use, and the first percentage of the first cannabinoid or the second percentage of the second cannabinoid in conjunction with the at least one diagnosed condition of the patient;

presenting a human-readable display listing the preferred products and associated transactional data and product use recommendation data receiving, via a feedback mechanism, a patient input corresponding to the product use recommendation data and patient use data associated with use of a particular product of the preferred products, wherein the patient input is required prior to obtaining a new product from the preferred products and the patient input is associated with an effectiveness of the particular product relative to the at least one diagnosed condition of the patient;

determining, based on the patient input, the patient use data, and the first percentage of the first cannabinoid or the second percentage of the second cannabinoid, a modification to the data product model, wherein the modification comprises re-weighting the tags associated with an individual cannabinoid and terpene profile present in the particular product, and the modification contributes to selecting the preferred products from the one or more than one of the product data models;

propagating the re-weighting to other product data models of the one or more product data models that share the cannabinoid and terpene profile to contribute to a subsequent recommendation of the preferred products;

generating an update to a patient profile associated with the patient based on the patient use data; and transmitting the modification to the at least one connected data repository.

19. The method of claim 18, wherein the one or more product data models are selected based on an identification of a match between any information in the patient state diagnosis model and the one or more product data models.

20. The method of claim 19, wherein the one or more than one of the product data models from the connected data repository after no match was found and responsive to no match being found, an iterative search is conducted for a match until a match is found.

* * * * *